(12) United States Patent
Sanchez et al.

(10) Patent No.: US 9,295,389 B2
(45) Date of Patent: Mar. 29, 2016

(54) SYSTEMS AND METHODS FOR PRIMING AN INTRAOCULAR PRESSURE SENSOR IN AN INTRAOCULAR IMPLANT

(71) Applicant: Novartis AG, Basel (CH)

(72) Inventors: Robert Sanchez, Oceanside, CA (US); Michael Morelli, San Francisco, CA (US); Alex G. Fermin, Irvine, CA (US); Michael LeRoy Gelvin, Alta Loma, CA (US)

(73) Assignee: Novartis AG, Basel (CH)

( * ) Notice: Subject to any disclaimer, the term of this patent is extended or adjusted under 35 U.S.C. 154(b) by 142 days.

(21) Appl. No.: 14/094,884

(22) Filed: Dec. 3, 2013

(65) Prior Publication Data

US 2014/0171777 A1 Jun. 19, 2014

Related U.S. Application Data

(60) Provisional application No. 61/737,966, filed on Dec. 17, 2012.

(51) Int. Cl.
| | |
|---|---|
| *A61B 5/00* | (2006.01) |
| *A61B 3/16* | (2006.01) |
| *A61F 9/007* | (2006.01) |
| *A61B 5/03* | (2006.01) |

(52) U.S. Cl.
CPC ............... *A61B 3/16* (2013.01); *A61F 9/00781* (2013.01); *A61B 5/031* (2013.01)

(58) Field of Classification Search
CPC ............ A61B 3/00; A61B 3/16; A61B 3/165; A61B 3/18; A61B 3/185; A61B 5/031; A61B 5/0031; A61B 5/02014
See application file for complete search history.

(56) References Cited

U.S. PATENT DOCUMENTS

| | | |
|---|---|---|
| 4,089,329 A | 5/1978 | Couvillon, Jr. et al. |
| 4,206,762 A | 6/1980 | Cosman |
| 4,457,757 A | 7/1984 | Molteno |

(Continued)

FOREIGN PATENT DOCUMENTS

| | | |
|---|---|---|
| CN | 101360523 | 2/2009 |
| CN | 101466299 | 6/2009 |

(Continued)

OTHER PUBLICATIONS

International Searching Authority, International Search Report, PCT/US2012/66709, Apr. 19, 2013, 4 pages.

(Continued)

*Primary Examiner* — Max Hindenburg
(74) *Attorney, Agent, or Firm* — Haynes and Boone, LLP

(57) ABSTRACT

An IOP monitoring device for implantation in an eye of a patient may include a first tube having a first opening, the first tube being configured to extend into the anterior chamber. An intraocular pressure sensing (IOP) device for implantation in an eye of a patient may include a pressure sensor, a pressure sensor cap, and a tube coupled to a chamber inlet. The pressure sensor cap may include a recess having an inner surface, the recess configured to receive the pressure sensor such that a chamber is formed by the pressure sensor and the inner surface and a chamber inlet permitting a fluid to communicate with the chamber and be primed in a bubble-free manner. The tube may be coupled to the chamber inlet to allow fluid communication between an anterior chamber of the eye and the chamber.

20 Claims, 4 Drawing Sheets

(56) References Cited

U.S. PATENT DOCUMENTS

| | | |
|---|---|---|
| 4,560,375 A | 12/1985 | Schulte et al. |
| 4,604,087 A | 8/1986 | Joseph |
| 4,656,827 A | 4/1987 | Puillet |
| 4,750,901 A | 6/1988 | Molteno |
| 4,869,282 A | 9/1989 | Sittler et al. |
| 4,922,913 A | 5/1990 | Waters, Jr. et al. |
| 5,005,577 A | 4/1991 | Frenkel |
| 5,083,742 A | 1/1992 | Wylie et al. |
| 5,178,604 A | 1/1993 | Baerveldt et al. |
| 5,179,953 A | 1/1993 | Kursar |
| 5,397,300 A | 3/1995 | Baerveldt et al. |
| 5,433,701 A | 7/1995 | Rubinstein |
| 5,466,233 A | 11/1995 | Weiner et al. |
| 5,476,445 A | 12/1995 | Baerveldt et al. |
| 5,558,629 A | 9/1996 | Baerveldt et al. |
| 5,573,646 A | 11/1996 | Saito et al. |
| 5,626,558 A | 5/1997 | Suson |
| 5,681,275 A | 10/1997 | Ahmed |
| 5,702,618 A | 12/1997 | Saaski et al. |
| 5,707,643 A | 1/1998 | Ogura et al. |
| 5,722,948 A | 3/1998 | Gross |
| 5,891,097 A | 4/1999 | Saito et al. |
| 5,910,110 A | 6/1999 | Bastable |
| 6,007,511 A | 12/1999 | Prywes |
| 6,048,328 A | 4/2000 | Haller et al. |
| 6,050,970 A | 4/2000 | Baerveldt |
| 6,056,269 A | 5/2000 | Johnson et al. |
| 6,251,090 B1 | 6/2001 | Avery et al. |
| 6,261,256 B1 | 7/2001 | Ahmed |
| 6,443,893 B1 | 9/2002 | Schnakenberg et al. |
| 6,447,449 B1 | 9/2002 | Fleischman et al. |
| 6,468,283 B1 | 10/2002 | Richter et al. |
| 6,533,733 B1 | 3/2003 | Hylton et al. |
| 6,579,235 B1 | 6/2003 | Abita et al. |
| 6,589,198 B1 | 7/2003 | Soltanpour et al. |
| 6,682,500 B2 | 1/2004 | Soltanpour et al. |
| 6,712,764 B2 | 3/2004 | Jeffries et al. |
| 6,719,750 B2 | 4/2004 | Varner et al. |
| 6,726,676 B2 | 4/2004 | Stegmann et al. |
| 6,749,568 B2 | 6/2004 | Fleischman et al. |
| 6,939,299 B1 | 9/2005 | Petersen et al. |
| 6,962,573 B1 | 11/2005 | Wilcox |
| 6,976,982 B2 | 12/2005 | Santini, Jr. et al. |
| 7,025,740 B2 | 4/2006 | Ahmed |
| 7,137,952 B2 | 11/2006 | Leonardi et al. |
| 7,169,106 B2 | 1/2007 | Fleischman et al. |
| 7,252,006 B2 | 8/2007 | Tai et al. |
| 7,304,334 B2 | 12/2007 | Agarwal et al. |
| 7,354,416 B2 | 4/2008 | Quiroz-Mercado et al. |
| 7,409,863 B2 | 8/2008 | Bateman et al. |
| 7,544,176 B2 | 6/2009 | Rodgers et al. |
| 7,612,328 B2 | 11/2009 | Kaiser |
| 7,648,465 B2 | 1/2010 | Gordon |
| 7,756,559 B2 | 7/2010 | Abreu |
| 7,824,699 B2 | 11/2010 | Ralph et al. |
| 8,123,687 B2 | 2/2012 | Dacquay et al. |
| 8,182,435 B2 | 5/2012 | Dacquay et al. |
| 8,206,440 B2 | 6/2012 | Guarnieri |
| 8,257,295 B2 | 9/2012 | Rickard et al. |
| 8,419,673 B2 | 4/2013 | Rickard |
| 8,545,431 B2 | 10/2013 | Rickard |
| 8,549,925 B2 | 10/2013 | Tai et al. |
| 8,579,848 B2 | 11/2013 | Field et al. |
| 8,585,631 B2 | 11/2013 | Dacquay |
| 8,585,664 B2 | 11/2013 | Dos Santos et al. |
| 8,603,024 B2 | 12/2013 | Bohm et al. |
| 8,652,085 B2 | 2/2014 | Gelvin et al. |
| 8,721,580 B2 | 5/2014 | Rickard et al. |
| 8,753,305 B2 | 6/2014 | Field et al. |
| 8,814,820 B2 | 8/2014 | Bergheim et al. |
| 8,840,578 B2 | 9/2014 | Dos Santos et al. |
| 8,858,491 B2 | 10/2014 | Field et al. |
| 8,864,701 B2 | 10/2014 | Dos Santos et al. |
| 8,986,240 B2 | 3/2015 | Dos Santos et al. |
| 9,072,588 B2 | 7/2015 | Bohm et al. |
| 9,125,721 B2 | 9/2015 | Field |
| 9,132,034 B2 | 9/2015 | Dos Santos |
| 2001/0000527 A1 | 4/2001 | Yaron et al. |
| 2002/0013545 A1 | 1/2002 | Soltanpour et al. |
| 2002/0013546 A1 | 1/2002 | Grieshaber Hans R. et al. |
| 2002/0019607 A1 | 2/2002 | BUI |
| 2002/0049374 A1 | 4/2002 | Abreu |
| 2002/0087111 A1 | 7/2002 | Ross et al. |
| 2002/0099359 A1 | 7/2002 | Santini, Jr. et al. |
| 2002/0103412 A1 | 8/2002 | Trimmer |
| 2002/0139947 A1 | 10/2002 | Wang |
| 2002/0143284 A1 | 10/2002 | Tu et al. |
| 2002/0156413 A1 | 10/2002 | Williams et al. |
| 2002/0156461 A1 | 10/2002 | Joshi |
| 2002/0165478 A1 | 11/2002 | Gharib et al. |
| 2002/0169468 A1 | 11/2002 | Brown |
| 2002/0175191 A1 | 11/2002 | Joshi et al. |
| 2002/0193674 A1 | 12/2002 | Fleischman et al. |
| 2003/0014036 A1 | 1/2003 | Varner et al. |
| 2003/0078487 A1 | 4/2003 | Jeffries et al. |
| 2003/0225318 A1 | 12/2003 | Montegrande et al. |
| 2003/0234376 A1 | 12/2003 | Cabuz et al. |
| 2004/0013702 A1 | 1/2004 | Glover |
| 2004/0059248 A1 | 3/2004 | Messner et al. |
| 2004/0073137 A1 | 4/2004 | Lloyd John R. et al. |
| 2004/0073156 A1 | 4/2004 | Brown |
| 2004/0111050 A1 | 6/2004 | Smedley et al. |
| 2004/0116794 A1 | 6/2004 | Fink et al. |
| 2004/0186367 A1 | 9/2004 | Fresco |
| 2004/0228734 A1 | 11/2004 | Jeon et al. |
| 2004/0254438 A1 | 12/2004 | Chuck et al. |
| 2004/0254517 A1 | 12/2004 | Quiroz-Mercado et al. |
| 2005/0016866 A1 | 1/2005 | Kramer et al. |
| 2005/0049578 A1 | 3/2005 | Tu et al. |
| 2005/0067029 A1 | 3/2005 | Henning et al. |
| 2005/0159660 A1 | 7/2005 | Montegrande et al. |
| 2005/0271704 A1 | 12/2005 | Tu et al. |
| 2005/0273033 A1 | 12/2005 | Grahn et al. |
| 2006/0041220 A1 | 2/2006 | Boukhny et al. |
| 2006/0131350 A1 | 6/2006 | Schechter et al. |
| 2006/0189916 A1 | 8/2006 | Bas |
| 2007/0019156 A1 | 1/2007 | Fink |
| 2007/0032757 A1 | 2/2007 | Medow et al. |
| 2007/0077270 A1 | 4/2007 | Wen |
| 2007/0106199 A1 | 5/2007 | Krivoy et al. |
| 2007/0106200 A1 | 5/2007 | Levy |
| 2007/0109117 A1 | 5/2007 | Heitzmann et al. |
| 2007/0123767 A1 | 5/2007 | Montegrande et al. |
| 2007/0129623 A1 | 6/2007 | Fleischman et al. |
| 2007/0156079 A1 | 7/2007 | Brown |
| 2007/0212397 A1 | 9/2007 | Roth |
| 2007/0243111 A1 | 10/2007 | Momose |
| 2007/0255262 A1 | 11/2007 | Haase |
| 2008/0015421 A1 | 1/2008 | Penner |
| 2008/0027478 A1 | 1/2008 | Connors et al. |
| 2008/0077127 A1 | 3/2008 | Gao et al. |
| 2008/0097276 A1 | 4/2008 | Bertrand et al. |
| 2008/0125691 A1 | 5/2008 | Yaron et al. |
| 2008/0129486 A1 | 6/2008 | Jeckelmann et al. |
| 2008/0147021 A1 | 6/2008 | Jani |
| 2008/0228127 A1 | 9/2008 | Burns et al. |
| 2008/0257915 A1 | 10/2008 | Wold |
| 2009/0069648 A1 | 3/2009 | Irazoqui et al. |
| 2009/0076367 A1 | 3/2009 | Sit et al. |
| 2009/0143713 A1 | 6/2009 | Van Dam et al. |
| 2009/0196903 A1 | 8/2009 | Kliman |
| 2009/0227933 A1 | 9/2009 | Karageozian |
| 2009/0240215 A1 | 9/2009 | Humayun et al. |
| 2009/0275924 A1 | 11/2009 | Lattanzio et al. |
| 2009/0312742 A1 | 12/2009 | Pang et al. |
| 2010/0010416 A1 | 1/2010 | Juan, JR. et al. |
| 2010/0042209 A1 | 2/2010 | Guarnieri |
| 2010/0114006 A1 | 5/2010 | Baerveldt |
| 2010/0121248 A1 | 5/2010 | Yu et al. |
| 2010/0121348 A1 | 5/2010 | van der Burg et al. |
| 2010/0174272 A1 | 7/2010 | Weiner |
| 2010/0222769 A1 | 9/2010 | Meng et al. |
| 2010/0222770 A1 | 9/2010 | Gordon et al, |
| 2010/0234717 A1 | 9/2010 | Wismer |

(56) References Cited

U.S. PATENT DOCUMENTS

| | | | |
|---|---|---|---|
| 2010/0249691 A1 | 9/2010 | Van Der Mooren et al. |
| 2010/0253167 A1 | 10/2010 | Charnley et al. |
| 2010/0280349 A1 | 11/2010 | Dacquay et al. |
| 2010/0305550 A1 | 12/2010 | Meng et al. |
| 2011/0007454 A1 | 1/2011 | Tang |
| 2011/0046536 A1 | 2/2011 | Stegmann et al. |
| 2011/0071454 A1 | 3/2011 | Dos Santos et al. |
| 2011/0071456 A1 | 3/2011 | Rickard |
| 2011/0071458 A1 | 3/2011 | Rickard |
| 2011/0071459 A1 | 3/2011 | Rickard et al. |
| 2011/0071505 A1 | 3/2011 | Rickard et al. |
| 2011/0077626 A1 | 3/2011 | Baerveldt et al. |
| 2011/0082385 A1 | 4/2011 | Diaz et al. |
| 2011/0144617 A1 | 6/2011 | Meng et al. |
| 2011/0203700 A1 | 8/2011 | Scholten et al. |
| 2011/0248671 A1 | 10/2011 | Dos Santos et al. |
| 2011/0282328 A1 | 11/2011 | Ambati et al. |
| 2012/0004528 A1 | 1/2012 | Li et al. |
| 2012/0022505 A1 | 1/2012 | Dacquay et al. |
| 2012/0022506 A1 | 1/2012 | Rickard et al. |
| 2012/0039770 A1 | 2/2012 | Namkoong et al. |
| 2012/0296258 A1 | 11/2012 | Rickard et al. |
| 2012/0302861 A1 | 11/2012 | Marshall et al. |
| 2012/0316492 A1 | 12/2012 | Chappel |
| 2013/0000765 A1 | 1/2013 | Fernandes et al. |
| 2013/0085440 A1 | 4/2013 | Bohm et al. |
| 2013/0144202 A1 | 6/2013 | Field et al. |
| 2013/0150774 A1 | 6/2013 | Field et al. |
| 2013/0150775 A1 | 6/2013 | Dos Santos et al. |
| 2013/0150777 A1 | 6/2013 | Bohm et al. |
| 2013/0150778 A1 | 6/2013 | Dos Santos |
| 2013/0158381 A1 | 6/2013 | Rickard |
| 2013/0204177 A1 | 8/2013 | Field et al. |
| 2013/0211311 A1 | 8/2013 | Field |
| 2013/0211312 A1 | 8/2013 | Gelvin |
| 2013/0218064 A1 | 8/2013 | Rickard |
| 2013/0317413 A1 | 11/2013 | Field et al. |
| 2013/0338564 A1 | 12/2013 | Rickard et al. |
| 2014/0039374 A1 | 2/2014 | Dos Santos et al. |
| 2014/0107557 A1 | 4/2014 | Dos Santos et al. |
| 2014/0163448 A1 | 6/2014 | Lind et al. |
| 2014/0166140 A1 | 6/2014 | Santos et al. |
| 2014/0171777 A1 | 6/2014 | Sanchez et al. |
| 2014/0172090 A1 | 6/2014 | Gunn |
| 2015/0057523 A1 | 2/2015 | Gunn |
| 2015/0057592 A1 | 2/2015 | Gunn |
| 2015/0057593 A1 | 2/2015 | Johnson et al. |
| 2015/0057595 A1 | 2/2015 | Gunn et al. |
| 2015/0057596 A1 | 2/2015 | Lind et al. |
| 2015/0150720 A1 | 6/2015 | Gunn et al. |
| 2015/0230982 A1 | 8/2015 | Gunn et al. |
| 2015/0230984 A1 | 8/2015 | Gunn |

FOREIGN PATENT DOCUMENTS

| | | |
|---|---|---|
| DE | 4438201 | 5/1996 |
| EP | 0102747 | 3/1984 |
| EP | 1195523 | 4/2002 |
| EP | 1917987 | 5/2008 |
| JP | 03049775 | 8/1992 |
| JP | 2005535392 | 11/2005 |
| JP | 2007512866 | 5/2007 |
| WO | WO9303665 | 3/1993 |
| WO | WO9803665 | 1/1998 |
| WO | WO9803809 | 1/1998 |
| WO | WO9938470 | 8/1999 |
| WO | WO0174427 | 10/2001 |
| WO | WO0194784 | 12/2001 |
| WO | WO02056758 | 7/2002 |
| WO | WO03001991 | 1/2003 |
| WO | WO03102632 | 12/2003 |
| WO | WO2004014218 | 2/2004 |
| WO | WO2005079204 | 9/2005 |
| WO | WO2005088417 | 9/2005 |
| WO | WO2007127305 | 11/2007 |
| WO | WO2007136993 | 11/2007 |
| WO | WO2008060649 | 5/2008 |
| WO | WO2008061043 | 5/2008 |
| WO | WO2008084350 | 7/2008 |
| WO | WO2008094672 | 8/2008 |
| WO | WO2009010799 | 1/2009 |
| WO | WO2009026499 | 2/2009 |
| WO | WO2009049686 | 4/2009 |
| WO | WO2009081031 | 7/2009 |
| WO | WO2010129446 | 11/2010 |
| WO | WO2010136071 | 12/2010 |
| WO | WO2011034727 | 3/2011 |
| WO | WO2011034738 | 3/2011 |
| WO | WO2011034740 | 3/2011 |
| WO | WO2011034742 | 3/2011 |
| WO | WO2011035218 | 3/2011 |
| WO | WO2012012017 | 1/2012 |
| WO | WO2013052332 | 4/2013 |
| WO | WO2013058943 | 4/2013 |
| WO | WO2013085894 | 6/2013 |
| WO | WO2013085895 | 6/2013 |
| WO | WO2013090006 | 6/2013 |
| WO | WO2013090231 | 6/2013 |
| WO | WO2013123142 | 8/2013 |

OTHER PUBLICATIONS

International Searching Authority, Written Opinion of the International Searching Authority, PCT/US2012/66709, Apr. 19, 2013, 5 pages.

Byunghoon Bae, Hongseok Kee, Seonho Kim, Yeon Lee, Taeseok Sim, Yongkweon Him and Kyihwan Park; "In Vitro Experiment of the Pressure Regulating Valve for a Glaucoma Impact"; Journal of Micromechanics and Microengineering, 13 (2003); pp. 613-619.

Eggers, T., et al, "Wireless Intra-Ocular Pressure Monitoring System Integrated Into an Artificial Lens," 1st Annual Intl IEEE-Embs Special Topic Conference on Microtechnologies in Medicine & Biology, Oct. 12-14, 2000, pp. 466-469, Lyon, France.

Greene, M.E. and Gilman, B.G., "Intraocular Pressure Measurement With Instrumented Contact Lenses," Investigative Ophthalmology & Visual Science (IVOS), Apr. 1974, pp. 299-302, vol. 13, No. 4, IVOS.

Hjortdal, Jesper and Jensen, Peter, "In Vitro Measurement of Corneal Strain, Thickness, and Curvature Using Digital Image Processing," Acta Ophthalmologica Scandinavica, 1995, pp. 5-11, vol. 73, Denmark.

International Searching Authority, International Search Report, PCT/US2010/033329, Jul. 13, 2010, 4 pages.

International Searching Authority, Search Report and Written Opinion of the International Searching Authority, PCT/US2010/033329, Jul. 13, 2010, 8 pages.

International Searching Authority, International Search Report, PCT/US2010/047429, Nov. 1, 2010, 4 pages.

International Searching Authority, Written Opinion of the International Searching Authority, PCT/US2010/047429, Nov. 1, 2010, 7 pages.

International Searching Authority, International Search Report, PCT/US2010/047600, Dec. 14, 2010, 5 pages.

International Searching Authority, Written Opinion of the International Searching Authority, PCT/US2010/047600, Dec. 14, 2010, 7 pages.

International Searching Authority, International Search Report, PCT/US2010/049424, Nov. 26, 2010, 6 pages.

International Searching Authority, Written Opinion of the International Searching Authority, PCT/US2010/049424, Nov. 26, 2010, 8 pages.

International Searching Authority, International Search Report, PCT/US2011/036742, Aug. 17, 2011, 2 pages.

International Searching Authority, Written Opinion of the International Searching Authority, PCT/US2011/036742, Aug. 17, 2011, 5 pages.

Lam, Andrew K.C. and Douthwaite, William A., "The Effect of an Artificially Intraocular Pressure on the Central Corneal Curvature," Ophthalmic and Physiological Optics, 1997, pp. 18-24, vol. 17, No. 1, Elsevier Science, Ltd., Great Britain.

(56) References Cited

OTHER PUBLICATIONS

Leonardi, Matteo, et al., "A Soft Contact Lens With a Mems Strain Gage Embedded for Intraocular Pressure Monitoring," In Proc. 12th Int'l Conference on Solid State Sensors, Actuators and Microsystems, Jun. 8-12, 2003, pp. 1043-1046, vol. 2, Boston, MA.
Leonardi, Matteo, et al., "First Steps Toward Noninvasive Intraocular Pressure Monitoring with a Sensing Contact Lens," Investigative Ophthalmology & Visual Science (IVOS), 2004, pp. 3113-3117, vol. 45, No. 9, IVOS.
McLaren, Jay W., et al, "Continuous Measurement of Intraocular Pressure in Rabbits by Telemetry," Investigative Ophthalmology & Visual Science (IVOS), May 1996, pp. 966-975, vol. 37, No. 6, IVOS.
Puers, Robert, "Linking Sensors with Telemetry: Impact on the System Design," In Proc. 8th Int'l Conference of Solid State Sensors, Actuators, Eurosens, Jun. 25-29, 1995, pp. 169-174, Stockholm, Sweden.
Schnakenberg, U., et al, "Initial Investigations on Systems for Measuring Intraocular Pressure," Sensors and Actuators, 2000, p. 287-291, vol. 85, Elsevier Science B.V., Germany.
Stangel, Karsten, et al, "A Programmable Intraocular CMOS Pressure Sensor System Implant," IEEE Journal of Solid-State Circuits, Jul. 2001, pp. 1094-1100, vol. 36, No. 7, IEEE, Germany.
Ullerich, Stella, et al, "Micro Coils for an Advanced System for Measuring Intraocular Pressure," 1st Annual Int'l IEEE-EMBS Special Topic Conference on Microtechnologies in Medicine & Biology, Oct. 12-14, 2000, pp. 470-474, Lyon, France.
Van Schuylenbergh, K., et al, "An Implantable Telemetric Tonometer for Direct Intraocular Pressure Measurements," 1st European Conference on Biomedical Engineering, Feb. 1991, pp. 194-195, vol. 17, No. 20, Nice, France.
Walter, Peter; Intraocular Pressure Sensor: Where Are We—Where Will We Go? Journal Graefe's Archive for Clinical and Experimental Ophthalmology; Publisher Springer Berline/Heidelberg; ISSN 0721-832X (Print) 1435-702X (Online); Issue vol. 240, No. 5/May. 2002 DOI 10.1007/s00417-002-0474-y; pp. 335-336; Subject Collection Medicine.
Neagu Cristina R.; "A Medical Microactuator Based on an Electrochemical Principle"; Thesis at the Twente University,the Netherlands, Enschede; Aug. 28, 1998; pp. 1-162.
Saloomeh Saati M.D., et al.; "Mini Drug Pump for Ophthalmic Use"; TRANS Am Ophthalmol Soc 2009; 107; pp. 60-71.
Stemme et al.; "A Valveless Diffuser/Nozzle-Based Fluid Pump"; ScienceDirect; Sensors and Actuators A, 39; pp. 159-167 (1993).
Nisar, et al.; MEMS-Based Micropumps in Drug Delivery and Biomedical Applications; ScienceDirect; Sensors and Actuators B 130; pp. 917-942 (2008).
International Searching Authority, International Search Report, PCT US2010/047605; Dec. 16, 2010, 7 pages.
International Searching Authority, Written Opinion of the International Searching Authority, PCT US2010/047605; Dec. 16, 2010, 9 pages.
International Searching Authority, International Search Report, PCT/US2010/047612; Dec. 21, 2010, 7 pages.
Internationl Searching Authority, Written Opinion of the International Searching Authority, PCT/US2010/047612; Dec. 21, 2010, 10 pages.
Kuppermann B D et al., 2006, "Efficacy and safety of a novel intravitreous dexamethasone drug-delivery system after applicator or incisional placement in patients with macular edema", IOVS, 47 ARVO E-Abs 5913.
Miyamoto H et al., 1997, Biodegradable scleral implant for intravitreal controlled release of fluconazole, Curr Eye Res, 16(9), 930-935.
Mruthyunjaya P et al., 2003, "An intravitreal sustained release fluocinolone acetonide device to treat severe experimental uveitis", IOVS, 44, ARVO E-Abs 4215.
Ratanapakorn T et al., 2005, "Helical intravitreal triamcinolone implant: An explanation survival study", IVOS 46 E-Abs 484.
Rego MGR et al., 2004, "In vitro evaluation of sustained-release intravitreal dexamethasone implants", IOVS, 45 E-Abs 5060.
Sakurai E et al., 2001, "Scleral plug of biodegradable polymers containing ganciclovir for experimental cytomegalovirus retinitis", IOVS, 42(9), 2043-2048.
See R F et al., 2006, "Safety and drug release profile of injectable intravitreal sustained-release fluocinolone acetonide device", IOVS, 47, ARVO E-Abs 5119.
Tano R et al., 2005, Helical intravitreal implant: surgical method development and outcomes, IOVS, 46, ARVO E-Abs 483.
Varner S E et al., 2003, "Development of a minimally invasive intravitreal implant for drug delivery", IOVS, 44, ARVO E-Abs 4214.
Weiner A L, 2007, "Drug Delivery Systems in Ophthalmic Applications, In: Ocular Therapeutics; Eye on New Discoveries; T. Yorio, A. Clark, M.Wax, Eds, Elsevier Press/Academic Press, New York", pp. 7-43.
Yasukawa T et al., 2001, "Biodegradable scleral plugs for vitreoretinal drug delivery", Adv. Drug Del Rev., 52(1), 25-36.
International Searching Authority, International Search Report, PCT/US2013/026066, Apr. 17, 2013, 5 pages.
International Searching Authority, Written Opinion of the International Searching Authority, PCT/US2013/026066, Apr. 17, 2013, 8 pages.
Parkhutik, Vitali, et al., The Role of Hydrogen in the Formation of Porous Structures in Silicon, Materials Science & Engineering, 1999, B58, 95-99, Elsevier Science, S.A.
Dacquay, Bruno, Intraocular Pressure Sensor, Prosecution History, U.S. Appl. No. 12/434,709, filed May 4, 2009, 566 pages.
Rickard, Matthew J.A., Lumen Clearing Valve for Glaucoma Drainage Device, Prosecution History, U.S. Appl. No. 12/609,043, filed Oct. 30, 2009, 1507 pages.
Rickard, Matthew, Intraocular Pressure Sensor with External Pressure Compensation, Prosecution History, U.S. Appl. No. 12/563,244, filed Sep. 21, 2009, 562 pages.
Dos Santos, Cesario, Power Generator for Glaucoma Drainage Device, Prosecution History, U.S. Appl. No. 12/685,772, filed Jan. 12, 2010, 517 pages.
Dacquay, Bruno, Closed Loop Glaucoma Drug Delivery System, Prosecution History, U.S. Appl. No. 13/109,155, filed May 17, 2011, 238 pages.
Field, Leslie, Active Drainage Systems with Pressure-Driven Valves and Electronically-Driven Pump, Prosecution History, U.S. Appl. No. 13/315,329, filed Dec. 9, 2011, 1620 pages.
Rickard, Matthew J.A., Power Saving Glaucoma Drainage Device, Prosecution History, U.S. Appl. No. 12/837,803, filed Jul. 16, 2010, 1725 pages.
Dos Santos, Cecario P., Multilayer Membrane Actuators, Prosecution History, U.S. Appl. No. 13/315,905, filed Dec. 9, 2011, 1652 pages.
Rickard, Matthew, Intraocular Pressure Sensor with External Pressure Compensation, Prosecution History, U.S. Appl. No. 14/267,443, filed May 1, 2014, 53 pages.
Rickard, Matthew, Intraocular Pressure Sensor with External Pressure Compensation, Prosecution History, U.S. Appl. No. 13/565,907, filed Aug. 3, 2012, 1652 pages.
Barton, Keith, et al., "The Ahmed Baerveldt Comparison Study," Journal of Ophthalmology, Jul. 15, 2010, vol. 118, No. 3, Elsevier, Inc., USA.
International Searching Authority, Search Report of the International Searching Authority, PCT/US2012/057261, Jan. 23, 2013, 7 pages.
International Searching Authority, Written Opinion of the International Searching Authority, PCT/US2012/057261, Jan. 23, 2013, 8 pages.
International Searching Authority, International Search Report, PCT/US2014/039582, Oct. 22, 2014, 3 pages.
International Searching Authority, Written Opinion, PCT/US2014/039582, Oct. 22, 2014, 3 pages.
Mokwa et al., "Mircro-Transponder Systems for Medical Applications", IEEE Transactions on Instrumentation and Measurement, vol. 50, No. 6, Dec. 2001, 5 pgs.
International Search Report and Written Opinion issued for PCT/US2013/074148 dated Mar. 6, 2014, 8 pgs.

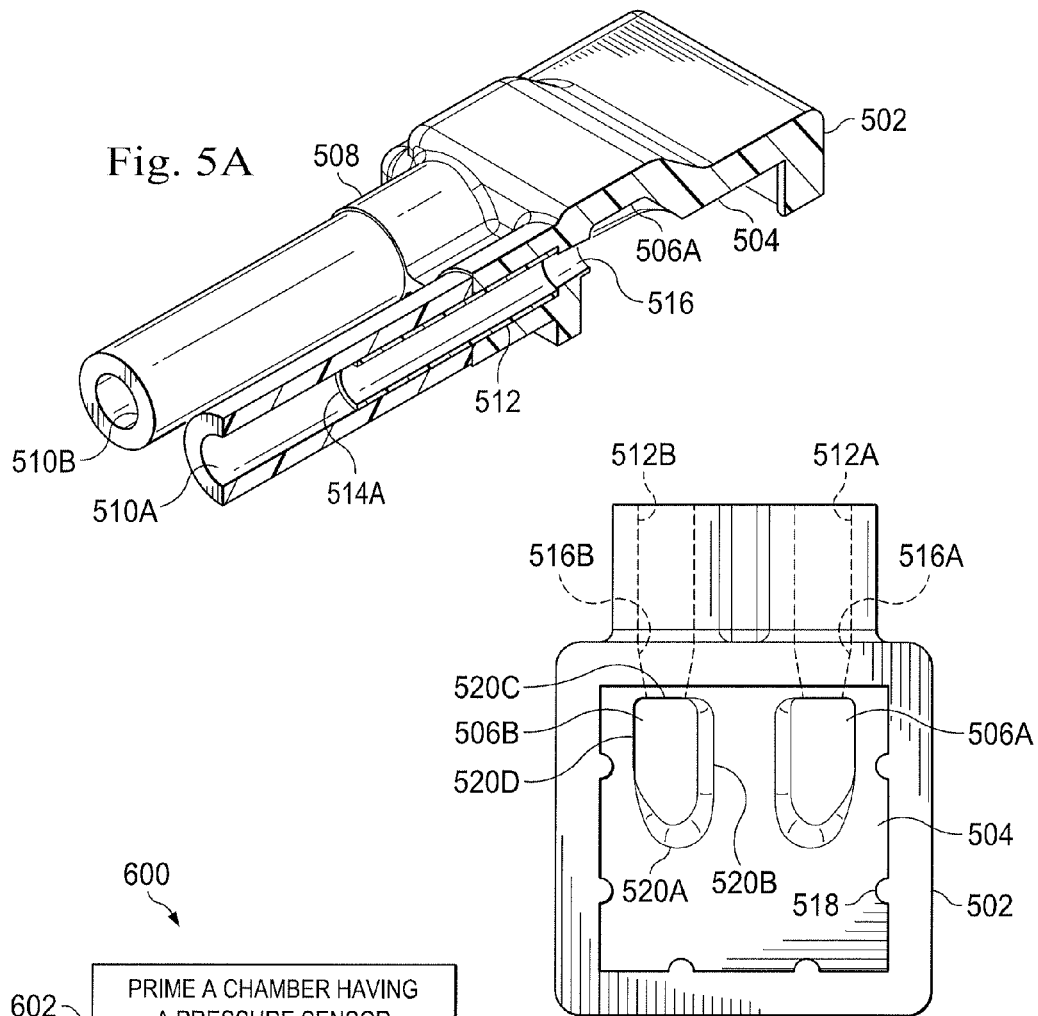
Fig. 5A
Fig. 5B
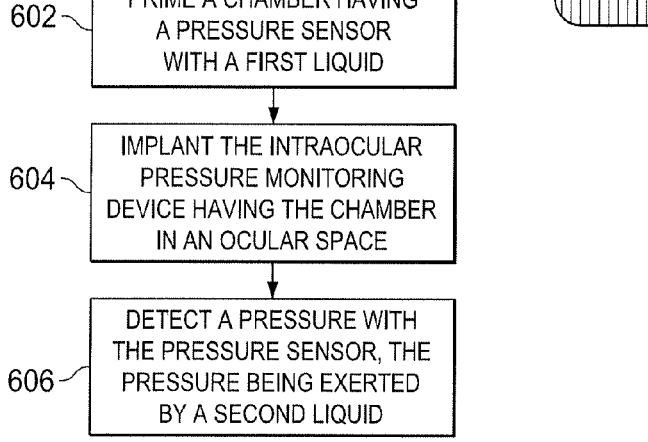
| 602 | PRIME A CHAMBER HAVING A PRESSURE SENSOR WITH A FIRST LIQUID |
| 604 | IMPLANT THE INTRAOCULAR PRESSURE MONITORING DEVICE HAVING THE CHAMBER IN AN OCULAR SPACE |
| 606 | DETECT A PRESSURE WITH THE PRESSURE SENSOR, THE PRESSURE BEING EXERTED BY A SECOND LIQUID |
Fig. 6

SYSTEMS AND METHODS FOR PRIMING AN INTRAOCULAR PRESSURE SENSOR IN AN INTRAOCULAR IMPLANT

PRIORITY CLAIM

This application claims the benefit of priority of U.S. Provisional Patent Application Ser. No. 61/737,966 titled "SYSTEMS AND METHODS FOR PRIMING AN INTRAOCULAR PRESSURE SENSOR IN AN INTRAOCULAR IMPLANT," filed on Dec. 17, 2012, whose inventors are Robert Sanchez, Michael Morelli, Alex G. Fermin, Michael LeRoy Gelvin, which is hereby incorporated by reference in its entirety as though fully and completely set forth herein.

BACKGROUND

The present disclosure relates generally to pressure measurement systems for use in ophthalmic treatments. In some instances, embodiments of the present disclosure are configured to be part of an intraocular implant comprising an intraocular pressure control system.

Glaucoma, a group of eye diseases affecting the retina and optic nerve, is one of the leading causes of blindness worldwide. Most forms of glaucoma result when the intraocular pressure (IOP) increases to pressures above normal for prolonged periods of time. IOP can increase due to high resistance to the drainage of the aqueous humor relative to its production. Left untreated, an elevated IOP causes irreversible damage to the optic nerve and retinal fibers resulting in a progressive, permanent loss of vision.

The eye's ciliary body continuously produces aqueous humor, the clear fluid that fills the anterior segment of the eye (the space between the cornea and lens). The aqueous humor flows out of the anterior chamber (the space between the cornea and iris) through the trabecular meshwork and the uveoscleral pathways, both of which contribute to the aqueous humor drainage system. The delicate balance between the production and drainage of aqueous humor determines the eye's IOP.

FIG. 1 is a diagram of the front portion of an eye that helps to explain the processes of glaucoma. In FIG. 1, representations of the lens 110, cornea 120, iris 130, ciliary body 140, trabecular meshwork 150, Schlemm's canal 160, and the edges of the sclera 170 are pictured. Anatomically, the anterior segment of the eye includes the structures that cause elevated IOP which may lead to glaucoma. Aqueous humor fluid is produced by the ciliary body 140 that lies beneath the iris 130 and adjacent to the lens 110 in the anterior segment of the eye. This aqueous humor washes over the lens 110 and iris 130 and flows to the drainage system located in the angle of the anterior chamber 180. The edge of the anterior chamber, which extends circumferentially around the eye, contains structures that allow the aqueous humor to drain. The trabecular meshwork 150 is commonly implicated in glaucoma. The trabecular meshwork 150 extends circumferentially around the anterior chamber. The trabecular meshwork 150 seems to act as a filter, limiting the outflow of aqueous humor and providing a back pressure that directly relates to IOP. Schlemm's canal 160 is located beyond the trabecular meshwork 150. Schlemm's canal 160 is fluidically coupled to collector channels (not shown) allowing aqueous humor to flow out of the anterior chamber. The sclera 170, the white of the eye, connects to the cornea 120, forming the outer, structural layer of the eye. The two arrows in the anterior segment of FIG. 1 show the flow of aqueous humor from the ciliary bodies 140, over the lens 110, over the iris 130, through the trabecular meshwork 150, and into Schlemm's canal 160 and its collector channels.

As part of a method for treating glaucoma, a doctor may implant a device in a patient's eye. The device may monitor the pressure in a patient's eye and facilitate control of that pressure by allowing excess aqueous humor to flow from the anterior chamber of the eye to a drainage site, relieving pressure in the eye and thus lowering IOP. To exert appropriate control, an accurate measurement of the pressure about the patient's eye may be made. However, accurately monitoring the pressure in the eye or pressure around the eye poses a number of difficulties. For example, pressure at locations spaced apart from the sensor location may be difficult to obtain, yet these may be useful in order to exert appropriate IOP regulation.

The system and methods disclosed herein overcome one or more of the deficiencies of the prior art.

SUMMARY

In one exemplary aspect, the present disclosure is directed to an intraocular pressure (IOP) monitoring device for implantation in an eye of a patient. The IOP monitoring device includes a pressure sensor and a pressure sensor cap. The pressure sensor cap includes a recess that has an inner surface and is configured to receive the pressure sensor such that a chamber is formed by the pressure sensor and the inner surface. At least one chamber inlet permits a fluid to communicate with the chamber. The IOP monitoring device further includes at least one tube coupled to at least one chamber inlet to allow fluid communication between an anterior chamber of the eye and the chamber.

In another exemplary aspect, a microfluidic pressure sensor system includes a housing having an inner surface that is configured to receive a pressure sensor, thereby forming a chamber. The housing is also configured to facilitate removal of gas bubbles from the chamber during introduction of a liquid into the chamber. An inlet portion of the housing permits fluid to enter the chamber; and a tube attachment portion of the housing allows a near end of a tube to attach to the inlet portion, thereby permitting a fluid at a far end of the tube to exert a pressure inside the chamber.

In yet another exemplary aspect, the present disclosure is directed to a method of treating an ocular condition. The method may include steps of priming a chamber in which a pressure sensor is located with a first liquid. The method also includes implanting an IOP monitoring device in an ocular space, the device having the pressure sensor in the chamber; and detecting a pressure exerted by a second liquid with the pressure sensor, the pressure being representative of a pressure of an anterior chamber of an eye.

It is to be understood that both the foregoing general description and the following drawings and detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following.

BRIEF DESCRIPTION OF THE DRAWINGS

The accompanying drawings illustrate embodiments of the devices and methods disclosed herein and together with the description, serve to explain the principles of the present disclosure.

FIG. 5A is a cross-sectional schematic diagram of an exemplary pressure sensor cap configured for connection with two tubes according to an exemplary aspect of the present disclosure.

FIG. 5B is a schematic diagram of an alternate view of the exemplary pressure sensor cap of FIG. 5A according to an exemplary aspect of the present disclosure.

FIG. 6 is a flowchart of a method for treating an ocular condition that may be performed using a pressure sensor and a pressure sensor cap, according to some embodiments.

DETAILED DESCRIPTION

Figure 1:
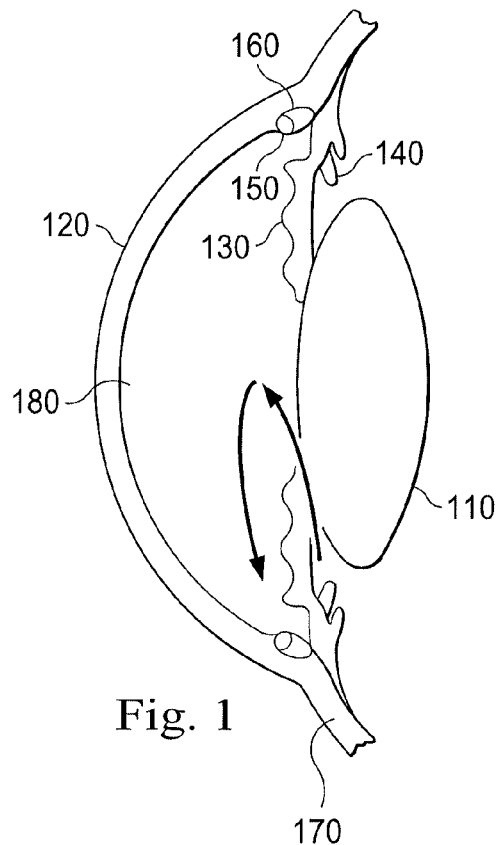
FIG. 1 is a cross-sectional diagram of the front portion of an eye.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates generally to a method and system for monitoring the intraocular pressure in a patient's eye and priming a pressure sensor for use in an intraocular pressure (IOP) monitoring device, such as a glaucoma drainage device (GDD). GDDs are used to alleviate excess pressure caused by aqueous humor accumulation in a patient's eye. The disclosed methods and systems may facilitate accurate pressure monitoring at a site removed from the pressure sensor. A pressure sensor cap may form a chamber with a pressure sensor. A tube connected to the pressure sensor cap may have an opening exposed to pressure at such sites. The pressure inside the chamber may correspond to the pressure at the tube opening, even though the chamber is disposed at a location spaced apart from the region being measured. Thus, the pressure measurement taken inside the chamber by the pressure sensor may correspond to the pressure at the site where the tube opening is placed. The systems and methods disclosed herein may thereby enable more accurate IOP determinations resulting in better information for determining treatment, potentially providing more effective treatment and greater customer satisfaction.

Figure 2:
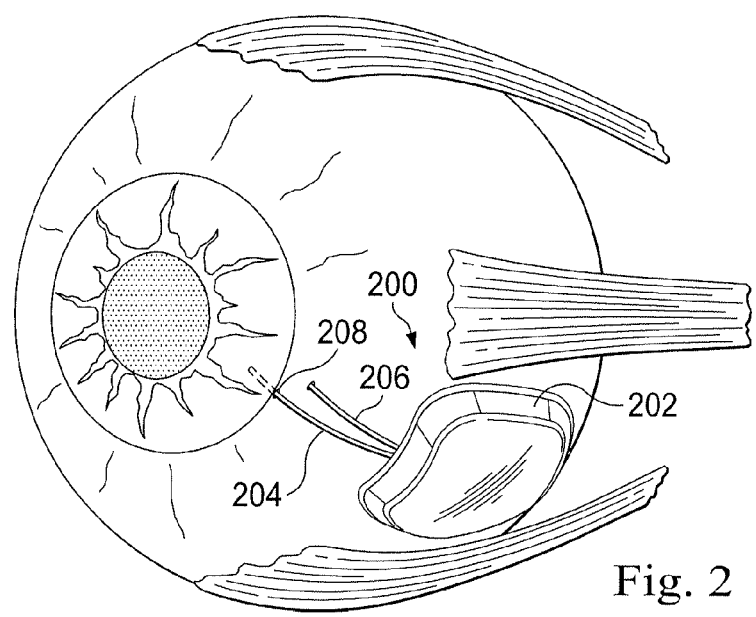
FIG. 2 is a schematic diagram of an eye and an ocular implant that carries an IOP monitoring system according to an exemplary aspect of the present disclosure.

FIG. 2 is a schematic diagram of an eye of a patient whose IOP is being monitored by an IOP monitoring device 200 shown as an ocular implant. The ocular implant may be a GDD. The IOP monitoring device 200 includes a plate 202, a pressure tube 204, and a drainage tube 206. The plate 202 may include or be arranged to carry various components of an IOP control system. In some embodiments, such components include a power source, a processor, a memory, a data transmission module, and a flow control mechanism (i.e. valve system). It may also carry one or more pressure sensor systems, which are described in greater detail below.

The plate 202 is configured to fit at least partially within the subconjunctival space and is sized within a range between about 15 mm×12 mm to about 30 mm×15 mm and has a thickness less than about 2 mm thick, preferably less than about 1 mm thick. The plate 202 may be formed to the radius of the eye globe (about 0.5 inches). It may be rigid and preformed with a curvature suitable to substantially conform to the globe or it may be flexible and can flex to conform to the globe. Some embodiments are small enough that conforming to the globe provides little benefit in comfort or implantation technique. The above dimensions are exemplary only, and other sizes and arrangements are contemplated herein.

In some embodiments, the pressure tube 204 extends from an anterior side of the plate 202 and is sized and arranged to extend into the anterior chamber of the eye through a surgically formed opening 208 in the sclera. In other embodiments, the pressure tubes extend to other locations about the eye where pressure measurements may be desired. The pressure tube 204 includes a first open end that may be disposed at a location where pressure measurements may be desired, and at least one lumen that extends to a second open end that may be disposed within or connected to the plate 202.

In some embodiments, the drainage tube 206 may also extend from an anterior side of the plate 202 of the IOP monitoring device 200. In such embodiments, the drainage tube 206 is used to allow excess aqueous humor to drain out of the anterior chamber of the eye, thereby relieving excess pressure. In some embodiments, the exterior surfaces of the pressure tube 204 and the drainage tube 206 are physically attached, thus providing little or no change to the surgical procedure for implantation of tube/plate glaucoma drainage devices. For the IOP monitoring device 200 to determine the pressure exerted by the aqueous humor within the anterior chamber, it may be advantageous to measure the pressure from outside the anterior chamber.

Figure 3A:
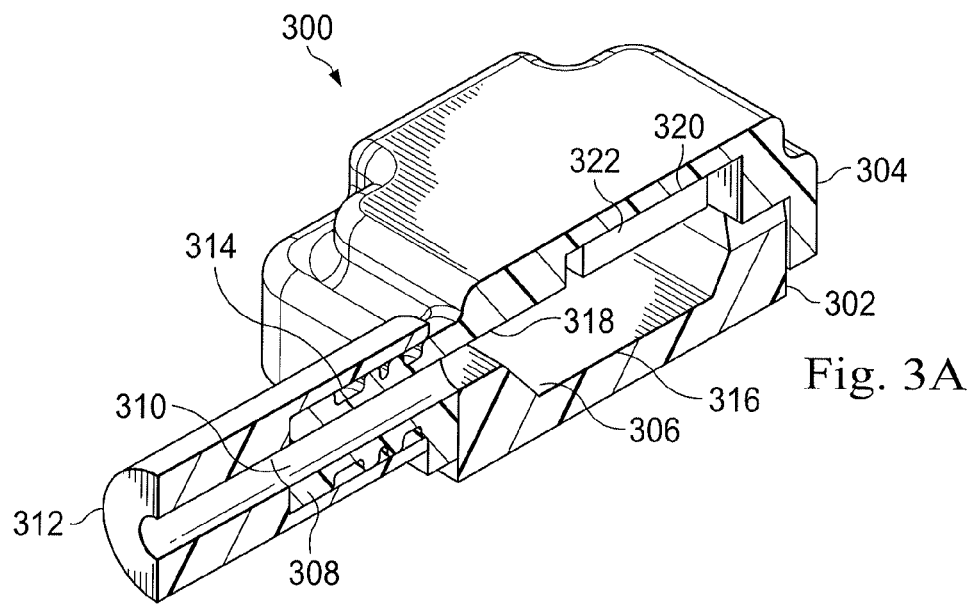
FIG. 3A is a cross-sectional schematic diagram of a pressure sensor and an exemplary pressure sensor cap as may be used in the IOP monitoring system according to an additional exemplary aspect of the present disclosure.

FIG. 3A is a pressure sensor system 300 that may be used within or as a part of the IOP monitoring device 200. The pressure sensor system 300 may allow a pressure sensor to detect pressures at locations spaced apart from the sensor itself. The pressure sensor system 300 includes a pressure sensor 302, which, in one exemplary embodiment, is a diaphragm-based sensor made from a semiconductor material such as silicon. Disposed over the pressure sensor 302 is a pressure sensor cap 304, which has a recess appropriately dimensioned to fit over the pressure sensor 302 and seal about the pressure sensor 302 so as to create a chamber 306. The pressure sensor 302 and the pressure sensor cap 304 may be attached with a biocompatible adhesive. In some embodiments, pressure sensor 302 and pressure sensor cap 304 are press fit together to create a seal. To allow access to the chamber 306, the pressure sensor cap 304 includes a tube attachment protrusion 308 which extends outward from a side of the pressure sensor cap 304 and includes a chamber-access hole 310 extending the full length of the tube attachment protrusion 308.

The chamber-access hole 310 serves as an inlet to the chamber permitting a fluid to communicate with the chamber 306. A tube 312 with a single lumen is depicted as attached to the tube attachment protrusion 308, with the lumen of the tube fluidically coupled to the chamber-access hole 308. In order for tube 312 to be coupled to the tube attachment protrusion 308, an attachment counterbore 314 may be provided therein, the counterbore 314 being sized relative to the tube attachment protrusion 308 so as to permit a seal to be formed therebetween. The seal may be a press-fit seal or may be formed by a biocompatible adhesive. Thus, access to the chamber 306 may be provided to a fluid only through the lumen of tube 312 and the chamber-access hole 310. Other embodiments have a lumen without the attachment counterbore 314. The tube 312 may be the same tube as tube 204 in FIG. 2.

The chamber 306 may be formed substantially by a bottom surface 316 (provided by the top of the pressure sensor 302) and a top surface 318 (provided by a bottom surface of the pressure sensor cap 304). As depicted in FIG. 3, the top surface 318 may include a recess 320. In one embodiment, the recess 320 is sized to accommodate a temperature sensor 322.

Figure 3B:
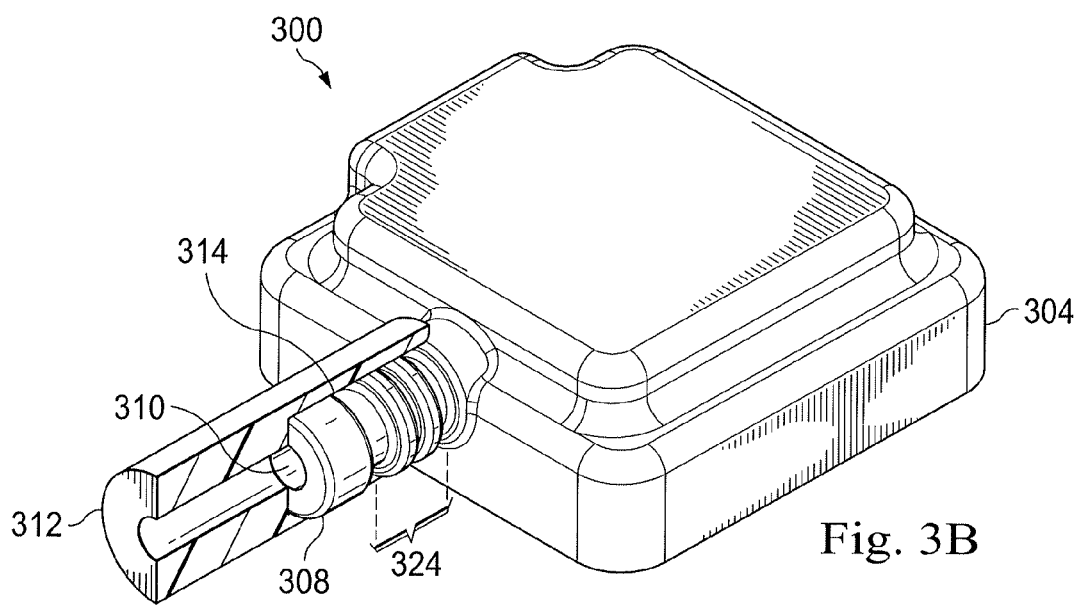
FIG. 3B is a schematic diagram of the exemplary pressure sensor cap according to an exemplary aspect of the present disclosure also seen in FIG. 3A.

FIG. 3B provides an alternative view of pressure sensor system 300. While the tube 312 is depicted in cross-section, the pressure sensor cap 304 is not. FIG. 3B thus provides an improved view of ridges 324 which form part of the external surface of tube attachment protrusion 308. Ridges 324 may provide contact surface for a secured and sealed coupling of the tube attachment portion 308 to the recess 314 of tube 312.

The pressure sensor system 300 may allow a pressure exerted by a gas at a remote end of the tube 312 to be measured inside the chamber 306 by the pressure sensor 302. For example, proper monitoring of a patient's eye disorder can require determining the IOP using an atmospheric reference pressure taken at a "dry" subconjunctival location. A "dry" location is a location spaced apart from an aqueous humor drainage site such that it is not influenced by the presence of aqueous humor at the drainage site. The dry location may be isolated from the drainage location by a patch graft, suturing down the conjunctiva or by some other means.

In the example shown, the pressure sensor cap 304 is depicted as being generally rectangular, however the pressure sensor cap 304 may be any shape, such as circular or ovoid. The pressure sensor 302 and the temperature sensor 322 may communicate data to other components of the IOP monitoring system 200. Using temperature sensor 322, the pressure sensor reading may be calibrated for temperature compensation increasing the precision and accuracy of the sensor readings. This data may be processed to provide information regarding the pressure being exerted at the distal end of the tube 312, and may be used by other components of the IOP monitoring device 200 to affect the pressure being exerted at another location. For example, the tube 312 may extend into the anterior chamber of the eye, into a drainage location, or to a location where a pressure representative of atmospheric pressure may be found. Since the tube opening is exposed in these areas, the pressure inside the chamber 306 corresponds to the pressure at the tube opening, even though the chamber 306 is disposed at a location spaced apart from the region being measured. Thus, the pressure measurement taken inside the chamber 306 by the pressure sensor 302 may correspond to the pressure at the opening of the tube 312.

Figure 4A:
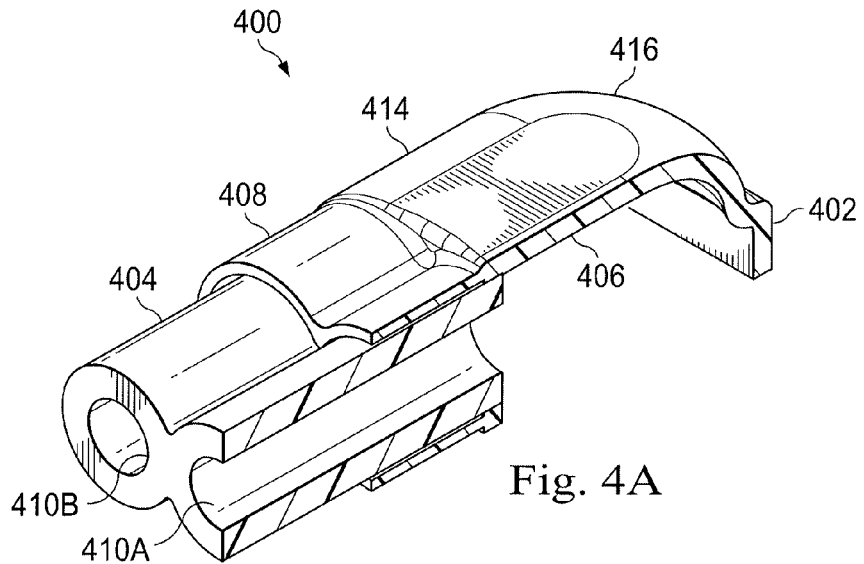
FIG. 4A is a cross-sectional schematic diagram of an exemplary pressure sensor cap configured to cooperate with a dual lumen tube according to an exemplary aspect of the present disclosure.
Figure 4B:
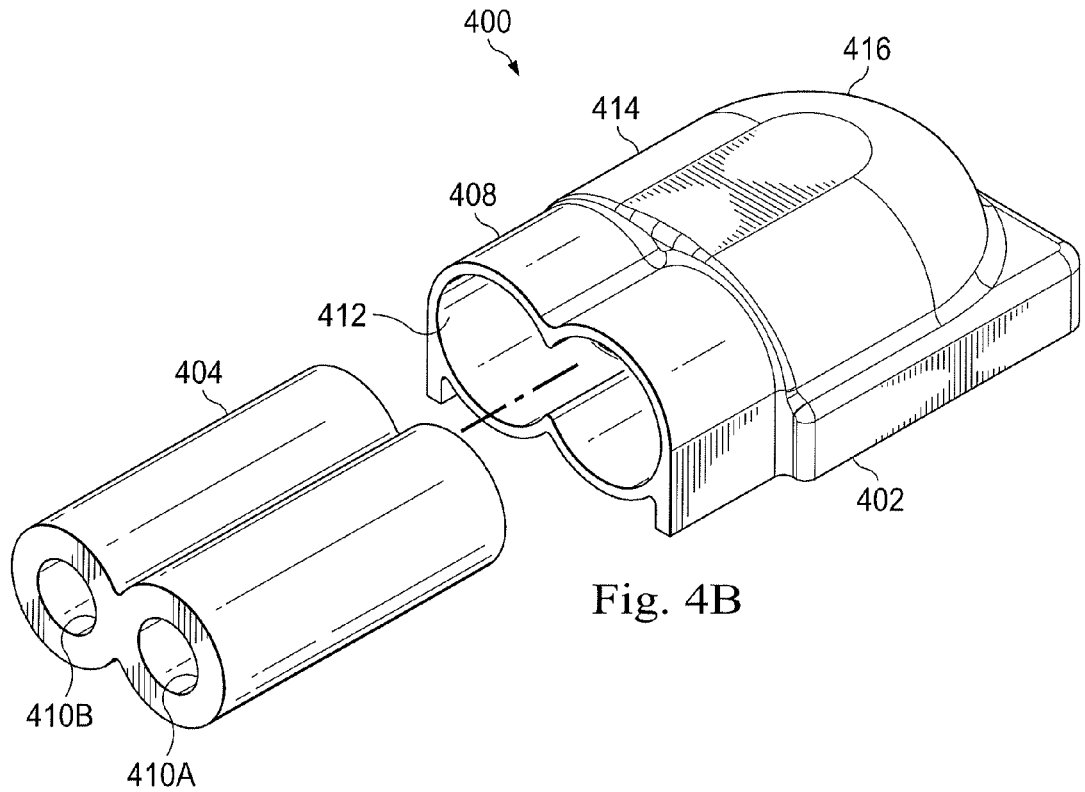
FIG. 4B is a schematic diagram of the exemplary pressure sensor cap of FIG. 4A not depicted in cross-section to show details of the exemplary aspect of the present disclosure.

FIGS. 4A and 4B are schematic diagrams of another pressure sensor system 400 that includes a pressure sensor cap, referenced herein by the numeral 402. Although a pressure sensor is not depicted, the pressure sensor cap 402 may receive and attach to a pressure sensor substantially as depicted and described with respect to pressure sensor 302 in FIG. 3A. FIG. 4A depicts the pressure sensor cap 402 in a cross-sectional view to highlight some important features. In the example in FIG. 4A, the pressure sensor cap 402 is coupled to a dual-lumen tube 404, which permits access to a chamber formed by an inner surface 406 of pressure sensor cap 402 and a pressure sensor (such as the pressure sensor 302) received therein (not depicted). The pressure sensor cap 402 has a tube attachment portion 408 which extends laterally from the chamber.

In the embodiment shown, the dual-lumen tube 404 is a pair of tubes joined or formed together and sharing a common outer surface. In the example shown, the dual-lumen tube 404 has a cross-section of two overlapping circles. Other embodiments may have two tubes attached at, or near, a tangent configuration. The dual-lumen tube 404 may be formed in a variety of configurations having dual lumens, referenced herein as a first lumen 410A and a second lumen 410B. For example, in some embodiments, the dual-lumen tube 404 is a single tube structure, having two equally-sized lumens 410A and 410B, and in other embodiments, the dual-lumen tube 404 is a single tube with differently-sized lumens 410A and 410B therein. Furthermore, the exterior surface shape of the dual lumen may vary. In some embodiments, the outer surface is as shown, as two overlapping circles, while in other embodiments, the outer surface is formed as a single circle or some other shape. Regardless of the tube shape, the tube may be formed in a manner allowing it to mate with the tube attachment portion 408 of the pressure sensor cap 402.

In the embodiment in FIGS. 4A and 4B, the tube attachment portion 408 has an opening or hole 412 therethrough, which has a cross-section that receives the tube 404. In this embodiment, the cross-section is substantially identical to the cross-section of the dual-lumen tube 404. Thus, the cross-section of the hole 412 also has the shape of two overlapping circles. This may be best seen in FIG. 4B, which shows the pressure sensor cap 402 in schematic view with the dual-lumen tube 404 withdrawn from hole 412. The dual-lumen tube 404 and the pressure sensor cap 402 may be securely coupled by nature of a close fit between these two components and/or adhesives or other methods. The tubes 404 may be the tubes 204 and 206 in FIG. 2.

The inner surface of the pressure sensor cap 402 is shaped to provide accurate pressure readings when the cap 402 is cooperatively combined with a pressure sensor, such as the pressure sensor 302. In the embodiment depicted, the pressure sensor cap 402 has a substantially cylindrical portion 414, which may have a cylindrical or ovoid cross-section. Pressure sensor cap 402 may also have a substantially hemispherical portion 416 at a side of the pressure sensor cap opposite that of the tube attachment portion 408. In general, neither hemispherical portion 416 nor cylindrical portion 414 may be perfectly hemispherical or cylindrical. Rather these features may have shapes similar to that of a hemisphere or cylinder. The intersection of these two portions is smooth and un-interrupted by sharp angles or acute angles.

The shape of the inner surface 406 is designed to minimize or eliminate sites at which small or microscopic bubbles of gas may adhere when a liquid is circulated through the chamber, by avoiding sharp corners in the chamber. That is, the shape of the inner surface 406 of the pressure sensor cap 402 is designed to prevent small gas bubbles from remaining inside the chamber. The gas bubbles are compressible and can act as a buffer to the pressures exerted outside the chamber and may decrease the accuracy of pressure measurements made within the cap 402. By preventing the small gas bubbles from adhering to surfaces of the chamber, substantially all of the gas may be removed, thereby providing more accurate measurements of the pressure exerted by the liquid at the distant end of the dual-lumen tube 404.

In operation, a saline or other sterile, biocompatible solution may be injected into the chamber formed by a pressure sensor cap 402 and a pressure sensor 302 through one lumen, either 410A or 410B of the dual-lumen tube 404. As the volume of liquid injected into the chamber through the lumen increases, gas will be forced from the chamber through the other lumen of the dual-lumen tube 404. The pressure sensor cap 402 may be made of a biocompatible plastic such as polyether ether ketone (PEEK) to prevent adverse biochemical reactions from occurring. Additionally, the pressure sensor 302 may be coated with a biocompatible coating, such as a thin layer of vapor deposited parylene C, parylene HT, or parylene X.

FIG. 5A depicts an embodiment of pressure sensor system that includes a pressure sensor cap 502. Pressure sensor cap 502, may be molded or machined from PEEK or another biocompatible material, and has a recess suitable to receive a pressure sensor, such as pressure sensor 302, to form a chamber. The chamber may have a top surface 504 that has a pair of flow directing recesses 506A and 506B, 506A being depicted in cross-section in FIG. 5A. More detail will be provided later regarding the flow directing recesses 506A and 506B. Pressure sensor cap 502 has a tube attachment portion 508 that protrudes from a side of the pressure sensor cap 502. The tube attachment portion 508 may have two hollow cylindrical portions provided for connecting to two tubes 510A and 510B. Tubes 510A-B may abut the two cylindrical portions of tube attachment portion 508. In some embodiments, tube 510A is adhesively attached to one of the two cylindrical portions, while tube 510B is adhesively attached to the other of the two cylindrical portions. One or both of the tubes 510A-B may be the tube 204 in FIG. 2.

As depicted in FIG. 5A, the two cylinder portions of tube attachment portions 508, which both have holes therethrough, each include a recess formed as a counterbore, either counterbore 512A or counterbore 512B, that extends part way through the tube attachment portion 508. The counterbore 512A extends from the opening of one of the two cylinder portions to a nozzle 516A at the chamber side.

As can be seen, an attachment insert 514A extends within the tube 510A and the tube attachment portion 508. The inner diameter of the counterbore 512A is, in this embodiment, equal to an outer diameter of the attachment insert 514A, which is positioned partially within the counterbore, with the rest of the attachment insert positioned within the lumen of tube 510A. An additional attachment insert (referenced herein as "514B", but not shown in FIG. 5A because tube 510B is not shown in cross-section), like attachment insert 514A, may be used to securely attach tube 510B and the counterbore 512B in tube attachment portion 508. Adhesives may be used to secure the attachment insert 514A to the counterbore 512A and the tube 510A. The attachment insert 514A, which may be made from a rigid material such as stainless steel, may also be press fit into both the counterbore 512A and the tube 510A.

A nozzle 516A or 516B connects each of the counterbores in the tube attachment portion 508 to one of the pair of flow directing recesses 506A and 506B. The nozzles 516A and 516B may be circular in cross-section, and may taper toward the chamber. That is, the nozzles may have a larger diameter on the end close to the attachment tubes 510A and 510B and a smaller diameter close to the flow directing recesses 506A and 506B. One embodiment includes one of the nozzles 516A, 516B tapering toward the chamber and the other nozzle of 516A, 516B tapering toward the tubes 510A or 510B (not shown). Fluid may travel through tube 510A, then through the tube attachment insert 514A, which may ensure the flow is properly directed, and finally through the nozzle 516A before reaching the flow directing recess 506A.

FIG. 5B is an alternate view of the pressure sensor cap 502 as seen looking at the inner surface. This view provides more detail regarding the flow directing recesses 506A and 506B, and depicts both nozzles 516A and 516B as well as recesses 512A and 512B. The flow directing recesses 506A and 506B are substantially symmetrical as seen in FIG. 5B. Therefore, description of one should be regarded as corresponding to the other.

Flow directing recess 506B has a shape that contacts top surface 504 at four main edges. The edges 520A, 520B, 520C, and 520D may meet each other at significantly rounded vertices, rather than abrupt angles. Edges 520A and 520B may be curved edges with respect to top surface 504, meaning that the associated sides of flow directing recess 506B curve into top surface 504. Edges 520C and 520D are sharp edges with respect to top surface 504, meaning that the associated sides of flow directing recess 506B do not curve into top surface 504, but meet it at an angle. In other embodiments, all the edges 520A-D may be curved, all the edges 520A-D may be straight, or some of edges 520A-D may be curved while others are straight.

The four edges 520A, 520B, 520C, and 520D form four angles at their vertices. As shown in FIG. 5B, edges 520A and 520B have an acute angle between them, edges 520B and 520C are joined at approximately a 90 degree angle, 520C and 520D also form an angle of approximately 90 degrees, and edges 520D and 520A form an obtuse angle.

FIG. 5B also depicts a plurality of side tabs, such as side tab 518, that may allow and promote secure attachment between the pressure sensor 302 and the pressure sensor cap 502. As depicted, pressure sensor cap 502 has two side tabs on each of the four main sidewalls which help form the large recess of the pressure sensor cap 502 that receives the pressure sensor 302. Other embodiments may have more or fewer side tabs 518.

In use, pressure sensor cap 502 may receive the pressure sensor 302 within the large recess formed by the top surface and the sidewalls. In addition to or in place of the plurality of tabs like tab 518, a biocompatible adhesive may be used to connect the pressure sensor cap 502 to the pressure sensor 302. In some embodiments, pressure sensor 302 may not be insertable into a pressure sensor cap, like pressure sensor cap 502. Instead, the pressure sensor 302 may be formed in a limited area on a substrate, which may include an application specific integration circuit (ASIC) or a system-on-chip device. The substrate may include pressure sensor 302, as well as a power source, a processor, memory, a data transmission module, and/or other components. When attached to the substrate, the pressure sensor cap 502 may not receive pressure sensor 302 into its large recess formed by the top surface and its four sidewalls. Instead, the pressure sensor cap 502 may be coupled to the surface of the substrate by an adhesive. In such embodiments, pressure sensor cap 502 may not have sidewalls, but may be a substantially flat surface, adhesively joined to the surface of the substrate above the limited area occupied by pressure sensor 302. The flat surface may be substantially similar to top surface 504, having two flow directing recesses 506A and 506B. The pressure sensor caps 402 and 302 may likewise be modified for use with a pressure sensor 302 incorporated in an ASIC. In such embodiments, the top surface of the pressure sensor cap is otherwise as described.

The pressure sensor 302 may be able to determine different pressures depending on the positioning of the tubes connected to it by pressure sensor caps 304, 402, or 502. For instance, if the tubes are inserted through the sclera 170 into the anterior chamber 180 of the eye as shown in FIG. 2, a pressure reading may be obtained that reflects the pressure in the anterior chamber 180. Additionally, if the tubes are placed underneath a piece of sutured pericardium or a scleral graft (not shown in FIG. 2) to isolate them under the subconjunctival space, a pressure may be obtained in such a location that is related to atmospheric pressure. The difference between the measured anterior pressure and the measured atmospheric pressure would then relate to the IOP.

In embodiments using multiple tubes or multiple lumens, the pressure tube may also be used as the drainage tube. In such embodiment, the drainage may flow through one of the two tubes or lumens from the anterior chamber of the eye to the pressure chamber 306 that houses the pressure sensor 302. The fluid may continue to flow out of the chamber 306 through the other of the two tubes or lumens and then through valves, pumps, or through an exit port from the GDD to a drainage site. Since there is flow present, appropriate fluid algorithms may be used to calculate the true pressure in the anterior chamber.

FIG. 6 is a flowchart of a method 600 for treating an ocular condition that may be performed using a pressure sensor and a pressure sensor cap such as disclosed in FIGS. 4A-B and 5A-B and discussed above. The method may allow a pressure exerted at a remote, distal opening of a tube to be used to exert a pressure inside a pressure chamber to facilitate measurement of the pressure even while being removed from the source of the pressure. The method may begin at 602 when a chamber having a pressure sensor located therein is primed with a first liquid. In 604, an intraocular pressure monitoring device, which has the pressure sensor and the chamber, may be implanted in an ocular space. Finally, in 606, the pressure sensor in the IOP monitoring device may be used to detect a pressure exerted by a second liquid. The pressure may represent the pressure of an anterior chamber of a patient's eye, drainage site pressure, atmospheric pressure, or other pressure.

In practice, the method 600 may be performed in the following manner using pressure sensor cap 502 of FIGS. 5A and 5B. The pressure chamber may be primed using any number of methods. In one example, a user, such as a health care provider, may couple a syringe filled with saline solution to a distal end of tube 510A. Compressing the syringe may force the fluid through tube 510A and through attachment insert 514A. The attachment insert 514A may also ensure that the solution enters the nozzle 516A on axis, rather than off axis. This may reduce flow separation effects resulting in fewer bubbles trapped in the chamber after the priming step is complete. The solution may continue to flow from nozzle 512 into the flow directing recess 506A and into the chamber formed by the pressure sensor cap 502 and the pressure sensor 302. As the chamber fills, the solution begins to flow through the flow directing recess 506B before passing through nozzle 512B, attachment insert 514B, and out through tube 510B. As the solution passes along this path, it displaces air or inert gases, and bubbles of the air or inert gases, that previously occupied the space in the chamber and tubes. The shape, along with the rounded edges and surfaces in the pressure sensor cap 502 may inhibit or prevent bubbles of air of the inert gases from attaching to the inner surfaces of the chamber. Priming may be performed during manufacturing or in preparation for surgery.

After priming the chamber, the pressure sensor system may be implanted as part of an IOP monitoring device or GDD, as indicated at 604. An exemplary implantation technique may include forming a small opening 208 in the eye to allow the ends of tube 510A and 510B to be inserted into an anterior chamber 180 of a patient's eye as discussed in connection with FIG. 2. After insertion into the eye, the saline solution with which the chamber and tubes were primed will contact and intermix with the aqueous humor of the anterior chamber 180. The pressure exerted by the aqueous humor on the anterior chamber 180 will be transferred by the fluid through tubes 510A and 510B to the pressure sensor 302, which may detect and measure the pressure within the anterior chamber. In some embodiments, the measurements made by the IOP monitoring device 200 may be used in diagnosing eye disorders. In some embodiments, the measurements may be used to control valves and other features within a GDD so that the pressure in the anterior chamber 180 may be lowered to and maintained at a desired level, thereby preventing harmful complications resulting from excess pressure, such as glaucoma.

In other embodiments, one lumen of the tube connects to a pressure location and the second lumen is redirected to an alternate location, such a fluid flow drainage path or a drainage site for example. In yet other embodiments, after the pressure sensor system is primed, one of the lumens or tubes may be sealed, leaving only a single tube or lumen extending to the desired pressure site. Sealing the tube may be performed, for example, by cutting the tube and sealing or closing it with heated forceps, plugging it with a cement or adhesive, ligating with a suture or other method.

The systems and methods disclosed herein may be used to provide increased accuracy in pressure measurements by permitting a user to obtain pressure data from a location spaced apart from the sensor location. Therefore, pressure at sensitive or difficult to access areas can be obtained and measured without implanting the entire sensor at that location. In addition, priming of the sensors can be more easily accomplished using dual lumen embodiments, including dual tube embodiments to remove bubbles that may affect the accuracy of the pressure readings. This may result in more effective treatment and more accurate data, thereby improving the overall clinical result.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

In some embodiments, a microfluidic pressure sensor system may include a housing having an inner surface configured to receive a pressure sensor, (thereby forming a chamber) and to facilitate removal of gas bubbles from the chamber during introduction of a liquid into the chamber. In some embodiments, a pressure sensor may be received in the housing. The microfluidic pressure sensor system may further include an inlet portion of the housing permitting fluid to enter the chamber and a tube attachment portion of the housing allowing a near end of a tube to attach to the inlet portion (thereby permitting a fluid at a far end of the tube to exert a pressure inside the chamber). The tube attachment portion may protrude from a side of the housing away from the recess. The microfluidic pressure sensor system may also include a temperature sensor recess in the inner surface, the sensor recess configured to receive a temperature sensor. In some embodiments, the tube attachment portion may have a hole therethrough. The hole may have an overlapping-circles-shaped cross-section (the cross-section being viewed orthogonally to an axis running through the center of the tube attachment portion). In some embodiments, the tube attachment portion has a hole therethrough, the hole being shaped to fittingly receive two circular tubes joined together at an outer surface the tubes. In some embodiments, the inner surface may have a substantially cylindrical portion connected to a substantially hemispherical portion. In some embodiments, the tube attachment portion includes two cylindrical tube connectors, the tube connectors each having a circular hole therethrough. A distal end of a first tube connector of the two cylindrical tube connectors may be configured to abut a proximal end of a first tube, and a distal end of a second tube connector may be configured to abut a proximal end of a second tube. Each of the tube connectors may include a circular recess extending partway along the circular hole therethrough. In some embodiments, the inlet portion may include two flow directors, the two flow directors being situated on the top surface. Each flow director may be a recess on the top surface coupled to the tube attachment portion on a side through a nozzle. In some embodiments, each flow director may have four edges at the top surface—a first adjacent two of the four edges may be rounded and form an acute angle with respect to each other and a second adjacent two of the four edges may not be rounded but form a generally right angle with respect to each other with one of the second adjacent edges being the closet of the four edges to the nozzle.

In some embodiments, a method of treating an ocular condition may include priming, with a first liquid, a chamber in which a pressure sensor is located, implanting an intraocular pressure (IOP) monitoring device in an ocular space (the device having the pressure sensor in the chamber) and detecting a pressure exerted by a second liquid with the pressure sensor (the pressure being representative of a pressure of an anterior chamber of an eye). In some embodiments, priming the chamber may include forcing the first liquid into the chamber through a tube connected to the chamber. The method may further include removing gas from the chamber through a second tube as the first liquid is forced into the chamber. Priming the chamber may include forcing the first liquid into the chamber through a first lumen of a dual lumen tube and removing gas from the chamber through a second lumen of the dual lumen tube. The method may further include connecting the tube to the anterior chamber of the eye (the anterior chamber containing the second liquid). Priming the chamber may include connecting a syringe to a distal end of a tube (a proximate end of the tube being connected to the chamber) and injecting the first liquid into the chamber through the tube until any gas present in the chamber has been removed through a second tube.

The invention claimed is:

1. An intraocular pressure (TOP) sensing device for implantation in an eye of a patient, comprising:
    a pressure sensor;
    a pressure sensor cap comprising:
        a recess having an inner surface, the recess configured to receive the pressure sensor such that a chamber is formed by the pressure sensor and the inner surface, and
        at least one chamber inlet permitting a fluid to communicate with the chamber; and
    at least one tube coupled to the at least one chamber inlet, the at least one tube allowing fluid communication between an anterior chamber of the eye and the chamber.

2. The TOP device of claim 1, further comprising a tube connection protrusion extending in an outward direction from a side of the pressure sensor cap, the chamber inlet being disposed in the tube connection protrusion.

3. The TOP device of claim 2, wherein the at least one tube is coupled to the at least one chamber inlet by inserting the tube connection protrusion into the at least one tube, and the tube connection protrusion has a hole therethrough.

4. The TOP device of claim 2, wherein the tube connection protrusion is configured to receive the at least one tube by insertion of the at least one tube into a hole extending through the tube connection protrusion to the chamber.

5. The TOP device of claim 1, wherein the at least one tube has a plurality of lumens therethrough.

6. The TOP device of claim 1, wherein the inner surface of the sensor cap comprises a top surface of the chamber, the top surface having a cylindrical portion and a hemispherical portion.

7. The TOP device of claim 3, wherein the hole through the tube connection protrusion has a cross-section in a shape of two overlapping circles.

8. The TOP device of claim 7, wherein the at least one tube comprises two tubes, the two tubes being joined together at an outer surface, the two tubes being jointly insertable into the tube connection protrusion.

9. The TOP device of claim 2, further comprising a rigid inner tube disposed in a proximal end of the at least one tube and in the tube connection protrusion in a manner that aligns the proximal end of the inner tube with the tube connection protrusion.

10. The TOP device of claim 2, wherein the at least one tube comprises two tubes and the at least one chamber inlet comprises two chamber inlets, one chamber inlet being associated with one tube, the tube connection protrusion having two holes therethrough, and wherein a proximal end of one of the two tubes is abuttingly connected to one of the two holes.

11. The TOP device of claim 10, wherein each of the two chamber inlets is a nozzle each nozzle having a smaller diameter at an end closer to the chamber.

12. The TOP device of claim 10, wherein the inner surface of the sensor cap comprises a top surface of the chamber, the top surface of the chamber comprising two flow directing recesses, each of the flow directing recesses configured to direct a liquid flowing through the chamber.

13. The TOP device of claim 11, wherein the inner surface of the sensor cap comprises a top surface of the chamber, the top surface of the chamber comprising two flow directing recesses, each flow directing recess being coupled on a side to one of the two chamber inlets, and each flow directing recess having four edges on the top surface, a first adjacent two of the four edges being rounded and forming an acute angle with respect to each other and a second adjacent two of the four edges not being rounded and forming a generally right angle with respect to each other, and one of the second adjacent edges is a closest edge to the nozzle.

14. The TOP device of claim 12, wherein the four edges of each of the two flow directing recesses are symmetrical with respect to an axis running in between the two flow directing recesses.

15. The TOP device of claim 1, wherein the inner surface of the pressure sensor cap is configured to facilitate removal of gas bubbles from the chamber during introduction of a liquid into the chamber.

16. An intraocular pressure (TOP) sensing device for implantation in an eye of a patient, comprising:
   a pressure sensor;
   a pressure sensor cap comprising:
      a recess having an inner surface, the recess configured to receive the pressure sensor such that a chamber is formed by the pressure sensor and the inner surface, and
      a plurality of chamber inlets permitting a fluid to communicate with the chamber; and
   a first tube and a second tube each coupled to one of the chamber inlets, the first tube allowing fluid communication between an anterior chamber of the eye and the chamber.

17. The TOP device of claim 16, further comprising a tube connection protrusion extending in an outward direction from a side of the pressure sensor cap, the chamber inlets being disposed in the tube connection protrusion.

18. The TOP device of claim 17, wherein the tube connection protrusion is configured to receive the first and second tubes by insertion into a hole extending through the tube connection protrusion to the chamber.

19. The TOP device of claim 18, wherein portions of the first and second tube that are inserted into the hole are parallel to each other.

20. The TOP device of claim 16, wherein the inner surface of the pressure sensor cap comprises a top surface of the chamber, the top surface having a cylindrical portion and a hemispherical portion.

* * * * *